United States Patent [19]

Smith

[11] Patent Number: 4,867,178

[45] Date of Patent: Sep. 19, 1989

[54] DISPOSABLE FACE SHIELD

[76] Inventor: B. Stewart Smith, 9016½ Pico Blvd., Los Angeles, Calif. 90035

[21] Appl. No.: 257,213

[22] Filed: Oct. 13, 1988

[51] Int. Cl.$^4$ ............................................... A61F 9/04
[52] U.S. Cl. .................................... 128/858; 128/863; 2/9; 2/12
[58] Field of Search ........... 128/857, 858, 863, 207.11; 2/9, 12, 206

[56] References Cited

U.S. PATENT DOCUMENTS

| | | | |
|---|---|---|---|
| 704,311 | 4/1902 | Galley | 2/174 |
| 865,484 | 9/1907 | Ellis | 2/12 |
| 1,075,667 | 10/1913 | Powers | 2/9 |
| 1,841,054 | 1/1932 | Powers | 2/9 |
| 2,141,972 | 12/1938 | Feiler | 128/863 |
| 2,360,482 | 10/1944 | Evans | 2/9 |
| 2,965,902 | 12/1960 | Louch | 2/9 |
| 4,080,664 | 3/1978 | Morris et al. | 128/206.15 |

Primary Examiner—Robert A. Hafer
Assistant Examiner—Lynda M. Cofsky
Attorney, Agent, or Firm—Philip D. Junkins

[57] ABSTRACT

A light-weight, disposable face shield assembly for the protection of the eyes and face of a wearer from accidental exposure to infectious, hazardous or undesirable substances. The shield assembly includes an elongated, semi-flexible head support strip divided into four foldable segments and a rectangular, semi-flexible, transparent protective face panel affixed at its upper edge portion to an intermediate face panel support segment of the head support strip. The intermediate face panel support segment is bounded on one side by a forehead support segment of shorter length than the face panel support segment and on the other side by first and second head support segments. Proximate the free end of the forehead support segment there is an assembly slot and at the fold line junction between the face panel support segment and the first head support segment there is a mating assembly slot whereby upon the interlocking of such slots the longer intermediate panel support segment is caused to bow outwardly in arcuate spaced orientation with respect to the forehead support segment. The free end portion of the second head support segment includes a series of equally spaced head strip sizing slots and at the fold line junction between the forehead support segment and the face panel support segment there is a mating assembly slot whereby upon the interlocking of a selected head strip sizing slot with the assembly slot of such fold line junction there is formed by the forehead support segment and the first and second head support segments an arcuate strip for surrounding the head of a wearer and for supporting the shield assembly on the wearer's head.

10 Claims, 1 Drawing Sheet

DISPOSABLE FACE SHIELD

FIELD OF THE INVENTION

The present invention relates to face shields for the protection of the eyes and face of wearers from accidental exposure to infectious, hazardous and undesirable substances. More particularly, the invention relates to anti-infection shields for the protection of health care workers and professionals and laboratory personnel from accidental exposure to infectious and/or hazardous and particulate materials.

BACKGROUND OF THE INVENTION

Health care workers have long recognized that caring for patients with certain infectious diseases poses risks of contracting such diseases. For example, many cases have been reported of accidental transmission of Hepatitus B from patients to persons involved in their care. More recently, the life threatening epidemic of Acquired Immunodeficiency Syndrome (AIDS) caused by the Human Immunodeficiency Virus (HIV) has aroused great concern. Although the bulk of the cases of patient to health care worker cross infection have resulted from accidental needlesticks, medical office, hospital, surgical, dental and laboratory personnel are now required to use extreme care in the handling of all patients and body fluids as potentially infected with HIV and other pathogens. Particular attention has been directed to the risk to surgeons and operating room personnel of infection through splashing or splattering of blood or other body fluids onto open wounds, into mouths or into the eyes of such personnel during the performance of surgical procedures.

Current recommendations of the Centers for Disease Control, Public Health Service of the U. S. Department of Health and Human Services concerning the prevention of HIV transmission in health care settings show an increasing concern for protection of the eyes (particularly conjunctiva) if aerosolization or splashing of blood or other fluids is likely to occur. Thus, according to the Centers for Disease Control, eye shields should be worn by medical personnel and laboratory workers to prevent blood and other body fluids from splattering into the eyes. An effective eye shield must protect the eyes no matter which direction the wearer faces. Ordinary eyeglasses are not sufficient protection.

It is an object of the present invention to provide a face shield for the protection of the eyes and face of wearers from accidental exposure to infectious, hazardous and undesirable substances.

It is another object of the invention to provide a face shield for the protection of health care workers and professionals and laboratory personnel from accidental exposure to body fluids from infected patients.

It is a further object of the invention to provide a low cost, disposable face shield for health care workers and professionals and laboratory personnel subject to accidental exposure to infectious fluids.

Another object of the invention is to provide a light-weight, protective face shield for a wide variety of workers who may be exposed to infectious, hazardous and undesirable substances.

Still another object of the invention is to provide a light-weight, disposable protective face shield which is readily formed up from a flat packaged form and may be worn over ordinary eyeglasses.

Other objects and advantages of the invention will become apparent from the following summary and detailed description of preferred embodiments of the invention taken in conjunction with the accompanying drawing figures.

SUMMARY OF THE INVENTION

The present invention relates to a light-weight, disposable face shield for the protection of the eyes and face of wearers from accidental exposure to infectious, hazardous and undesirable substances. It is of particular interest in the protection of health care workers and professionals and laboratory personnel from accidental exposure to body fluids from infected patients. The shield includes essentially: an elongated, semi-flexible and segmented head support strip; and a generally-rectangular, semi-flexible transparent eye/face protection panel. The transparent eye/face protection panel is affixed, in its upper edge portion, to an intermediate protection panel support segment of the head support strip. Extending laterally outward from the protection panel support segment of the head support strip, on one side of the protection panel, is a forehead support segment of the support strip. Extending laterally outward from the protection support segment of the support strip, on the other side thereof, is a first head support segment and thereafter a second head support segment with head size adjustment means.

The intermediate protection panel support segment of the head support strip and the adjoining first head support segment of such strip are of substantially equal length, are foldable together at their junction, and present at such junction an assembly slot extending downwardly of such junction from the top thereof to its midpoint. The forehead support segment of the head support strip is of shorter length than the adjoining intermediate protection panel support segment of such strip, such segments being foldable together at their junction and present at such junction an assembly slot extending upwardly of such junction from the bottom thereof to its midpoint. The outer free end of the shorter forehead support segment of the head support strip also includes an assembly slot (proximate the end of such segment) extending upwardly from the lower edge of the forehead support segment to its midpoint. The laterally extending first head support segment of the head support strip and the further extending second head support segment of the head support strip are foldable together at their junction. The second head support segment is of shorter length than the first head support segment and such second segment presents in its outermost portion a series of head size adjustment assembly slots extending downwardly from the upper edge of the second segment to its midpoint.

In its pre-use, flat-packaged and/or shield storage form, the disposable protective eye/face shield of the invention has the shorter forehead support segment of the head support strip folded inwardly so as to lie adjacent the intermediate protection panel support segment of the shield. The shorter second head support segment of the head support strip is also folded inwardly so as to lie adjacent the first head support segment of the head support strip and the so folded first and second head support segments are folded together inwardly so as to lie adjacent the forehead support segment of the head support strip.

To assemble the disposable face shield of the invention from its pre-use, flat-packaged and/or storage form the folded segments of the head support strip are unfolded. The slotted free end of the shorter forehead support segment of the strip is folded back and inwardly across the panel support segment to the mating assembly slot at the junction of the panel support segment and first head support segment and such slots are interlocked with the result that the shorter forehead support segment causes the longer panel support segment of the head support strip to bow outwardly from such shorter segment. The free end portion of the second head support segment of the head support strip (with the first head support segment) is folded back and inwardly across the panel support segment with one of the series of head size adjustment assembly slots of such second segment interlocked with the assembly slot at the junction (folded) of the panel support segment and forehead support segment of the head support strip. The portion of the free end of the second head support segment beyond the point of interlocking segment slots lies between the panel support segment and the forehead support segment of the assembled eye/face shield.

The panel support segment of the head support strip is provided with equally spaced score lines or fold lines so that such segment forms up in uniform spaced orientation from the forehead support segment of the head support strip. The first head support segment of the head support strip also is provided with one or more score lines or fold line so that such segment of the support strip is readily foldable with the second head support segment to form the sized head support strip when an assembly slot of the free end portion of the second segment is interlocked with the assembly slot at the fold junction of the panel support segment and forehead support segment of the head support strip. The second head support segment of the head support strip may be provided with appropriate indicia (series of head circumference measurement sizes) adjacent each of the head size adjustment assembly slots so that assembly of the eye/face shield may be readily accomplished with proper head support strip sizing. When the properly sized shield assembly is applied to the wearer's head, the normally-straight line or flat segments and segment portions of the head support strip will form into a relatively uniform arcuate strip surrounding the wearer's head in comfortable shield supporting fashion and the semi-flexible transparent protective panel of the shield (outwardly spaced from the head surrounding segments of the head support strip) forms into a somewhat arcuate shape so as to protect the front and sides of the wearer's face from accidental contact with infectious and/or hazardous and particulate materials.

BRIEF DESCRIPTION OF THE DRAWING FIGURES

DETAILED DESCRIPTION OF THE PREFERRED EMBODIMENT

Figure 3:
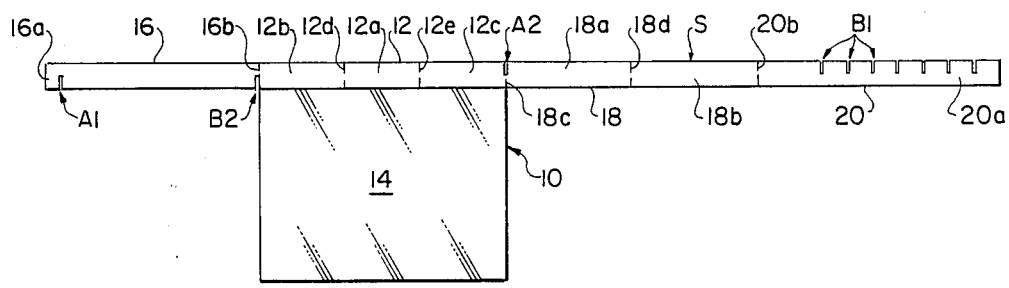
FIG. 3 is a rear view of the eye/face shield of the invention with the head support strip unfolded and ready for forming up the shield for use by a wearer.

Referring initially to FIG. 3 of the drawing there is illustrated a rear view of the light-weight, disposable face shield 10 of the invention in its fully-extended, unformed or preformed configuration. As shown, unformed shield 10 includes essentially: an elongated, semi-flexible head support strip S comprised of segments 12, 16, 18 and 20: and a generally-rectangular, semi-flexible transparent eye/face protection panel 14. The semi-flexible head support strip is formed of sheet plastic material or coated paper board. The semi-flexible transparent protection panel is formed of relatively thin optically clear plastic sheet material such as acetate or polyester plastic sheet material.

The transparent eye/face protection panel 14 is affixed at its upper edge portion (by any known means such as by adhesive material, heat sealing, riveting, etc.) to intermediate panel support segment 12 of the multi-segment head support strip S. Extending laterally outward from panel support segment 12, on one side (in FIG. 3 the left side) of the protection panel 14, is a forehead support segment 16 of the support strip. Extending laterally outward from the panel support segment 12, on the other side of the protection panel 14, is a first head support segment 18 and thereafter a second head support segment 20 with head size adjustment means.

The intermediate protection panel support segment 12 of the head support strip is comprised of three segment protions, i.e., center portion 12a and like side portions 12b and 12c defined with respect to such center portion by fold or score lines 12d and 12e. The forehead support segment 16 of the head support strip is of shorter length than the adjoining intermediate protection panel support segment 12 of such strip, such segments being foldable together at their junction 16b and present at such junction a shield assembly slot B2 extending upwardly of such junction from the bottom thereof to its midpoint. The intermediate protection panel support segment 12 of the head support strip and the adjoining first head support segment 18 of such strip are of substantially equal length, are foldable together at their junction 18c, and present at such junction a shield assembly slot A2 extending downwardly of such junction from the top thereof to its midpoint.

The outer free end 16a of the shorter forehead support segment 16 of the head support-strip also includes a shield assembly slot A1 (proximate the end of segment 16) extending upwardly from the lower edge of the forehead support segment 16 to its midpoint. The laterally extending first head support segment 18 of the head support strip and the further extending second head support segment 20 of such strip are foldable together at their junction 20b. The second head support segment 20 is of shorter length than the first head support segment 18 and such second segment presents in its outermost portion 20a a series of head size adjustment assembly slots B1 extending downwardly from the upper edge of such second segment to its midpoint.

Figure 1:
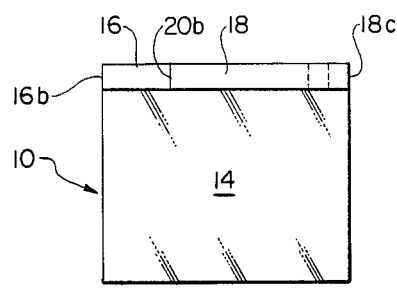
FIG. 1 is a rear view of the eye/face shield of the invention with the head support strip and transparent eye/face protection panel of the shield in its unformed, partially-folded orientation for flat compact packaging and/or storage.
Figure 2:
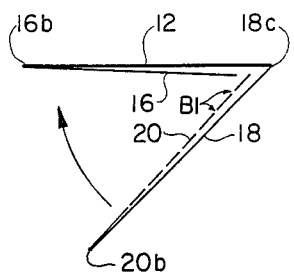
FIG. 2 is a top edge view of the eye/face shield of FIG. 1 showing the folded segments of the head support strip of the shield.

In its pre-use, flat-packaged and/or shield storage form as shown in FIGS. 1 and 2, the disposable protective eye/face shield 10 of the invention has the shorter forehead support segment 16 of the head support strip S folded inwardly so as to lie adjacent the intermediate protection panel support segment 12 of the shield. The short second head support segment 20 of the head support strip is also folded inwardly at junction line 20bso as to lie adjacent the first head support segment 18 of such strip and the so folded first and second head support segments are folded together inwardly at junction line 18c so as to lie adjacent the forehead support segment 16 of the head support strip S.

Figure 4:
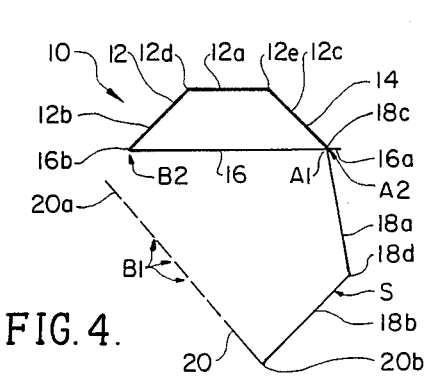
FIG. 4 is a top edge view of the eye/face shield of FIG. 3 showing the head support strip in its partially folded and assembled orientation ready for sizing before applying to a wearer's head.

To assemble the disposable face shield of the invention for use by a health care worker, medical professional, laboratory worker or other person having an eye/face protection need, the pre-use, flat-packaged form of the shield is opened, i.e., the head support strip segments are unfolded. The slotted free end 16a of the shorter forehead support segment 16 of the strip S is folded back and inwardly across the panel support segment 12 to the mating assembly slot A2 at the junction line 18c of the panel support segment and the first head support segment 18. The slot A1 (at the free end 16a of segment 16) is interlocked with the slot A2 at the junction line 18c with the result that the shorter forehead support segment 16 causes the longer panel support segment 12 of the head support strip S to bow outwardly from the shorter segment 16 as shown in FIG. 4. The outward bowing of the longer panel support segment 12 is aided by the fold or score lines 12d and 12e of segment 12.

Figure 5:
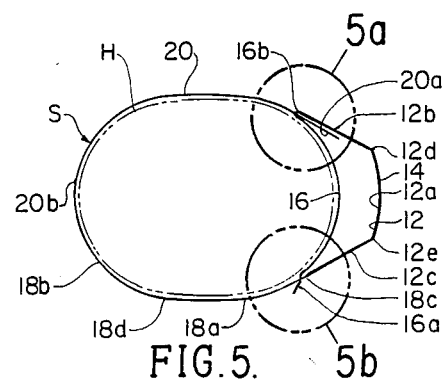
FIG. 5 is a top view of the eye/face shield of the invention in fully assembled (formed up) operative protective position on the wearer's head.
Figure 5A:
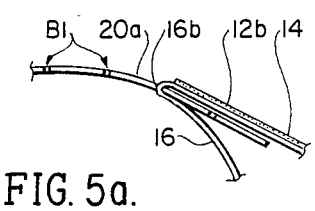
FIG. 5a is an enlarged-partial top view of the eye/face shield of FIG. 5 showing in detail the folded and assembled head support strip segments of the shield on the left side of the wearer's head at the edge of the transparent protection panel.
Figure 5B:
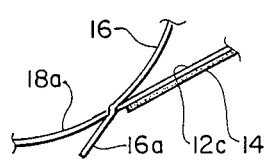
FIG. 5b is an enlarged partial top view of the eye/face shield of FIG. 5 showing in detail the folded and assembled head support strip segments of the shield on the right side of the wearer's head at the edge of the transparent protection panel.

The second head support segment 20 of the head support strip S (with the first head support segment 18) is folded back and inwardly across the panel support segment 12 (and forehead support segment 16) with one of the series of head size adjustment and shield assembly slots B1 in the free end portion 20a of such second segment interlocked with the assembly slot B2 at the junction line 16b (folded) of the panel support segment 12 and forehead support segment 16 of the head support strip S. The part of free end portion 20a of the second head support segment 20 extending beyond the point of interlocking of slot B2 with one of the slots B1 lies between the panel support segment 12 and the forehead support segment 16 of the assembled shield 10 as particularly shown in FIGS. 5 and 5a.

Figure 6:
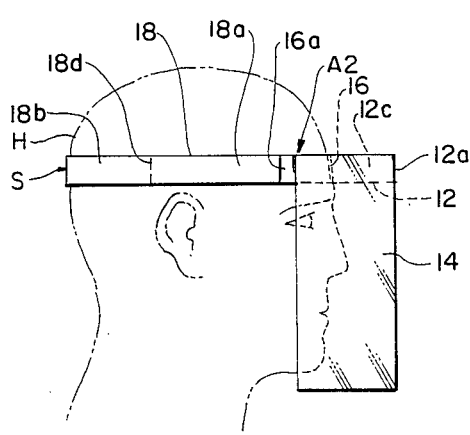
FIG. 6 is a side view of the eye/face shield of the invention in operative protective position on the head of a wearer of the shield.

As previously indicated, the panel support segment 12 of the head support strip S is provided with equally spaced score or fold lines 12d and 12e to assist in forming such segment outwardly of the forehead support segment 16 when slot A1 is interlocked with slot A2. The first head support segment 18 of the head support strip S is also provided with one or more score or fold lines 18d. Thus, such segment is divided into two or more segment portions 18a and 18b whereby head support segment 18 is readily foldable with the second head support segment 20 to form the sized head support strip S when an appropriate assembly slot B1 is interlocked with the assembly slot B2 at the fold junction 16b. The second head support segment 20 of the head support strip S is readily flexible because of the series of assembly slots B1 and thus easily forms into an arcuate shape about the head of the wearer (see particularly FIG. 5). Further, the second head support segment 20 of the head support strip S may be provided with appropriate indicia (series of head circumference measurement sizes) adjacent each of the head size adjustment assembly slots B1 so that assembly of the face shield 10 may be readily accomplished with proper head support strip sizing. When the properly sized shield assembly is applied to the wearer's head, the normally straight line or flat segments and segment portions of the head support strip S will form into a relatively uniform arcuate strip of segments surrounding the wearer's head (see FIG. 5) in comfortable ovate shield supporting fashion. The semi-flexible transparent protective panel 14 of the shield 10 (outwardly spaced from the head-surrounding segments 16, 18 and 20 of the head support strip S) forms into a somewhat arcuate shape so as to protect the front and sides of the wearer's face (see FIGS. 5 and 6) from accidental contact with infectious and/or hazardous liquids or particulate materials.

In the specification and drawing figures there has been set forth a preferred embodiment of a light-weight, disposable face shield for the protection of health care workers, medical professionals and laboratory personnel from accidental exposure to body fluids from virus infected individuals and from accidental exposure to other hazardous liquids or particulate materials, in accordance with the invention. Although specific terms have been employed in describing the invention, they are used in a generic and descriptive sense only and not for purposes of limitation, the scope of the invention being defined in the following claims.

What I claim is:

1. A light-weight, disposable face shield assembly for the protection of the eyes and face of a wearer from accidental exposure to infectious, hazardous or undesirable substances, said face shield assembly comprising:
   (a) an elongated, semi-flexible head support strip including a forehead support segment, an intermediate protective face panel support segment, a first head support segment and a second head support segment, the forehead support segment having a first free outer end and sharing a first foldable junction with the intermediate protective face panel support segment, the intermediate protective face panel support segment further sharing a second foldable junction with the first head support segment, the first head support segment further sharing a third foldable junction with the second head support segment, and the second head support segment further having a second free-outer end; the intermediate protective face panel support segment is of a greater length than said forehead support segment, and the first head support segment is of a greater length than said second head support segment;
   (b) a rectangular, semi-flexible, transparent protective face panel affixed at its upper edge portion to the intermediate protective face panel support segment of said head support strip and extending downwardly therefrom;

(c) first assembly means for said shield at the free outer end of the forehead support segment of said head support strip interlocking with first assembly means at the second junction of said panel support segment and said first head support segment whereby the shorter forehead support segment of said head support strip causes said longer intermediate panel support segment to bow outwardly in arcuate spaced orientation with respect to said forehead support segment; and (d) second assembly means for said shield at the free outer end of the second head support segment of said head support strip interlocking with second assembly means at the first junction of the forehead support segment and said panel support segment whereby the forehead support segment with the first head support segment and the second head support segment of said head support strip cooperate to form said segments into an arcuate strip for surrounding the forehead of a wearer and supporting said intermediate panel support segment with said affixed transparent protective face panel in arcuate spaced face protection orientation.

2. A light-weight, disposable face shield assembly as claimed in claim 1 wherein the first assembly means for said shield at the free outer end of the forehead support segment consists of a slot in said segment extending from the lower edge to the midpoint thereof and the first assembly means at the second junction of said panel support segment and said first head support segment consists of a slot extending from the top of said junction to the midpoint thereof, said slots interlocking to cause said longer intermediate panel support segment to bow outwardly in arcuate spaced orientation with respect to said forehead support segment.

3. A light-weight, disposable face shield assembly as claimed in claim 1 wherein the second assembly means for said shield at the free outer end of the second head support segment consists of a series of equally spaced slots in said segment extending from the upper edge to the midpoint thereof and the second assembly means at the first junction of the forehead support segment and said panel support segment consists of a slot extending from the lower end of said first junction to the midpoint thereof, one of said series of slots interlocking with the slot of said first junction to form the forehead support segment, the first head support segment and the second head support segment into said arcuate strip for surrounding the head of a wearer of said shield assembly and for sizing said arcuate strip to the wearer's head.

4. A light-weight, disposable face shield assembly as claimed in claim 3 wherein sequential head size indicia are printed on said second head support segment in association with the series of slots in said segment.

5. A light-weight, disposable face shield assembly as claimed in claim 1 wherein the elongated, semi-flexible head support strip of said face shield assembly is formed of a material selected from a group consisting of sheet plastic material or coated paper board.

6. A light-weight, disposable face shield assembly as claimed in claim 1 wherein the rectangular, semi-flexible, transparent protective face panel of said face shield assembly is formed of optically clear sheet material selected from a group consisting of an acetate plastic or a polyester plastic.

7. A light-weight, disposable face shield assembly for the protection of the eyes and face of a wearer from accidental exposure to infectious, hazardous or undesirable substances, said face shield assembly comprising:

(a) an elongated, semi-flexible head support strip including a forehead support segment, an intermediate protective face panel support segment, a first head support segment and a second head support segment, the forehead support segment having a first free outer end and sharing a first foldable junction with the intermediate protective face panel support segment, the intermediate protective face panel support segment further sharing a second foldable junction with the first head support segment, the first head support segment further sharing a third foldable junction with the second head support segment, and the second head support segment further having a second free-outer end; the intermediate protective face panel support segment is of a greater length than said forehead support segment, and the first head support segment is of a greater length than said second head support segment;

(b) a rectangular, semi-flexible, transparent protective face panel affixed at its upper edge portion to the intermediate protective face panel support segment of said head support strip and extending downwardly therefrom;

(c) first face shield assembly means at the free outer end of the forehead support segment consisting of a slot in said segment extending from the lower edge to the midpoint thereof and first face shield assembly means at the second junction of said panel support segment and said first head support segment consisiting of a slot extending from the top of said second junction to the midpoint thereof, said slots interlocking to cause said longer intermediate panel support segment to bow outwardly in arcuate spaced orientation with respect to said forehead support segment; and (d) second face shield assembly means at the free outer end of the second head support segment consiting of a series of equally spaced shield sizing slots in said segment extending from the upper edge to the midpoint thereof and second face shield assembly means at the first junction of the forehead support segment and said panel support segment consisting of a slot extending from the lower end of said first junction to the midpoint thereof, one of said series of shield sizing slots selected for interlocking with the slot of said first junction to form the forehead support segment, first head support segment and second head support segment into an arcuate strip for surrounding the head of a wearer and supporting said intermediate support segment with said affixed transparent protective face panel in arcuate spaced face protection orientation.

8. A light-weight, disposable face shield assembly as claimed in claim 7 wherein sequential head size indicia are printed on said second head support segment in association with the series of equally spaced shield sizing slots in said segment.

9. A light-weight, disposable face shield assembly as claimed in claim 7 wherein the elongated, semi-flexible head support strip of said face shield assembly is formed of a material selected from a group consisting of sheet plastic material or coated paper board.

10. A light-weight, disposable face shield assembly as claimed in claim 7 wherein the rectangular, semi-flexible, transparent protective face panel of said face shield assembly is formed of optically clear sheet material selected from a group consisting of an acetate plastic or a polyester plastic.

* * * * *